United States Patent [19]
Reisdorf et al.

[11] Patent Number: 5,103,817
[45] Date of Patent: Apr. 14, 1992

[54] AUTOMATIC DYE DISPERSANT FOR ENDOTRACHEAL TUBES AND CATHETERS

[75] Inventors: Dennis J. Reisdorf; James B. Hissong, both of Jacksonville, Fla.

[73] Assignee: Xomed-Treace Inc., Jacksonville, Fla.

[21] Appl. No.: 556,605

[22] Filed: Jul. 20, 1990

[51] Int. Cl.$^5$ .................. A61M 16/00; A62B 9/06
[52] U.S. Cl. .................. 128/207.15; 128/207.14; 604/97; 604/100; 604/111
[58] Field of Search .......... 128/207.15, 207.14, 128/200.26; 604/97, 100, 111

[56] References Cited

U.S. PATENT DOCUMENTS 4,834,087  5/1989  Coleman et al. ............ 128/207.14
4,953,548  9/1990  Stoddard et al. ............ 128/207.14

FOREIGN PATENT DOCUMENTS 0277797  8/1988  European Pat. Off. ....... 128/207.14

Primary Examiner—Edgar S. Burr
Assistant Examiner—Kimberly L. Asher
Attorney, Agent, or Firm—Stuart E. Krieger

[57] ABSTRACT

An indwelling device for passing fluids into or out of the body includes an inflatable cuff for lodging the device within a body passage. The inflatable cuff is inflated with a fluid such as saline. Prior to the inflation process a dye dispersant material such as methylene blue is incorporated in dry form within the inflation cuff and/or within an inflation lumen which leads to the inflation cuff and/or within a pilot balloon which is accessed by a source of saline fluid. Thus, as the cuff is inflated with saline, the methylene blue dissolves and disperses in the saline enabling the saline to take on the color of the methylene blue dye. A buffer is combined with the methylene blue to enhance the dispersal of the dye in the saline. Potential piercing of the expanded cuff after it is filled with methylene blue provides a blue stain or leak that is easily recognized as a sign of damage to the cuff. Correction steps can thus be taken to repair or replace the endotracheal tube as soon as the leak is recognized.

22 Claims, 4 Drawing Sheets

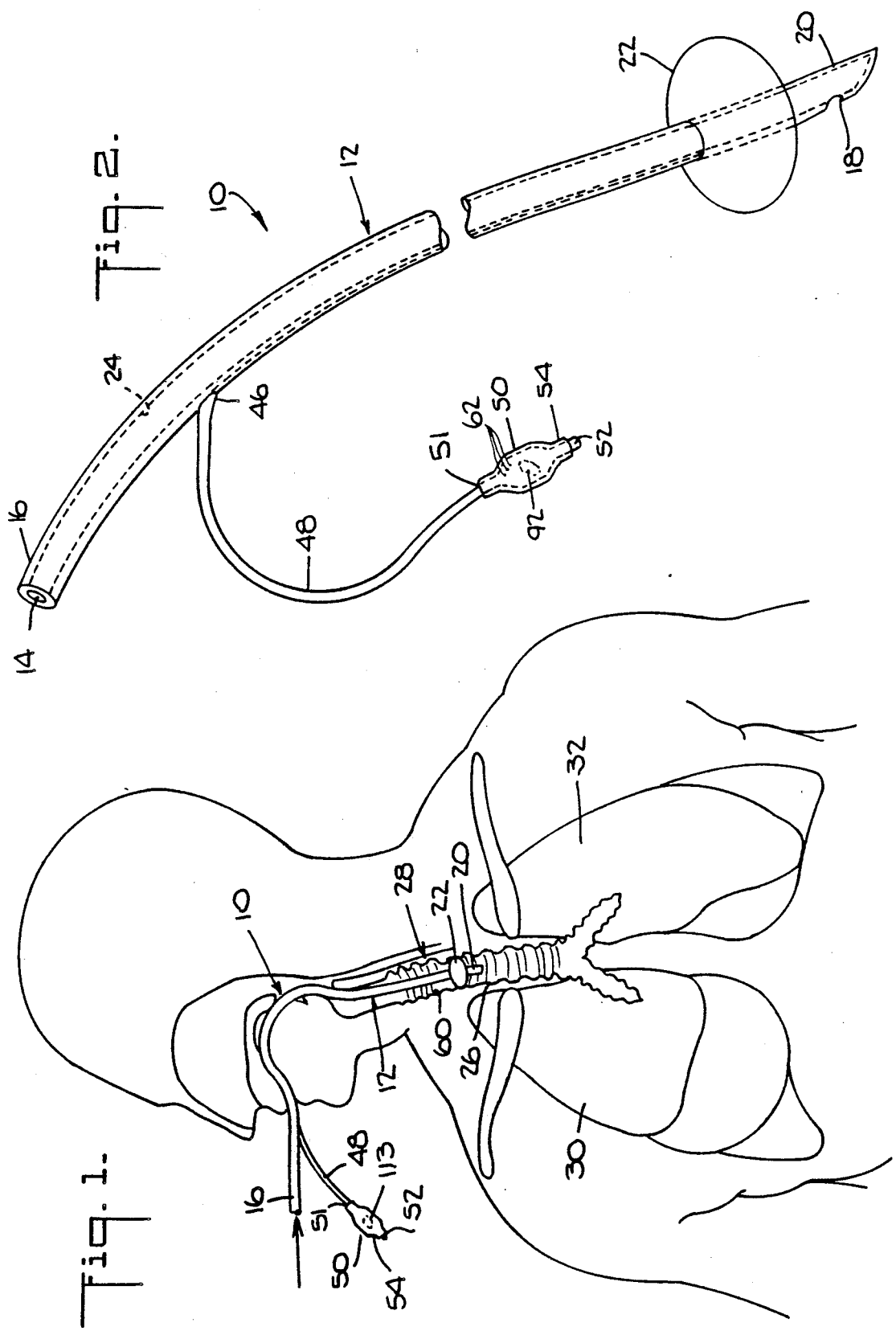

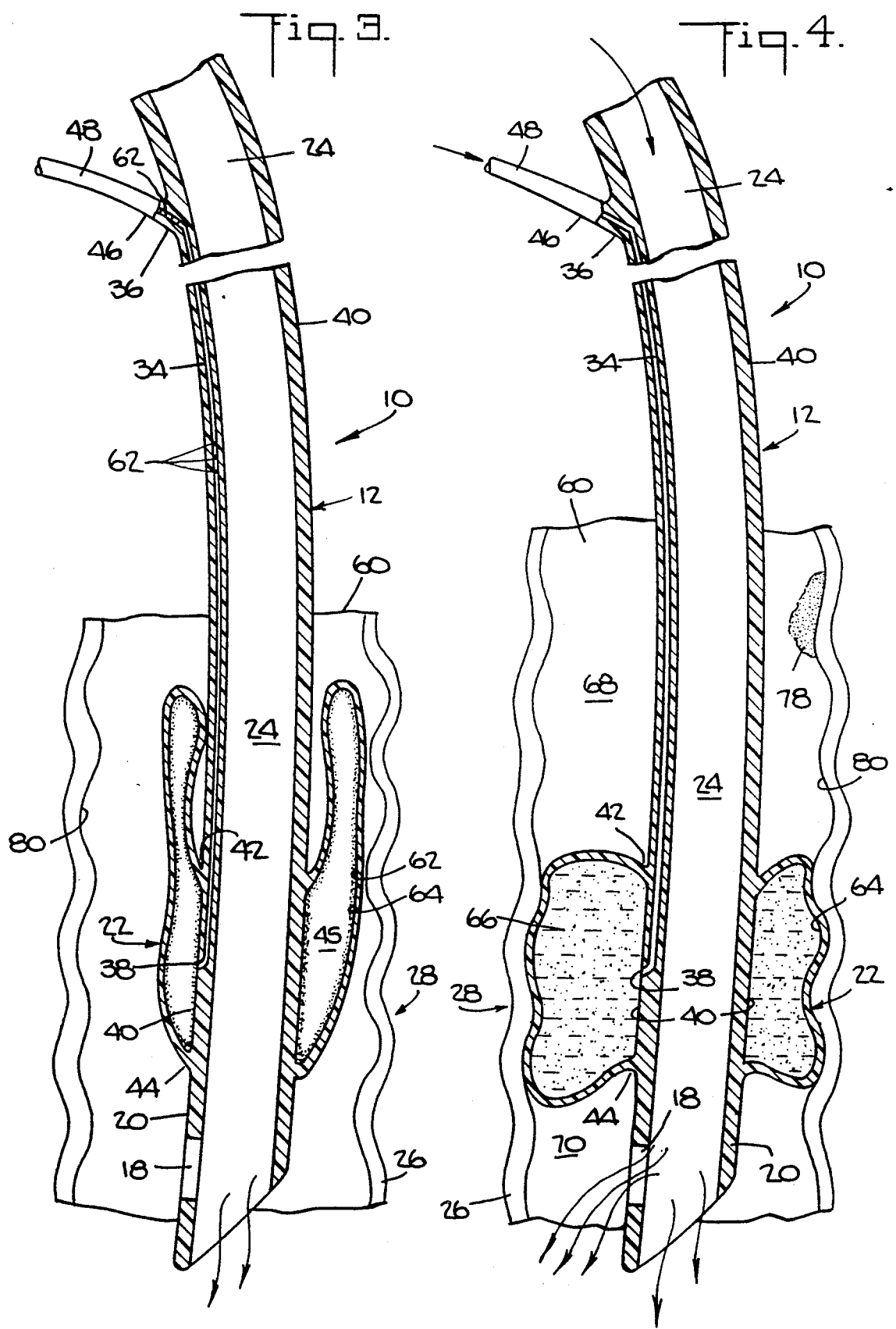

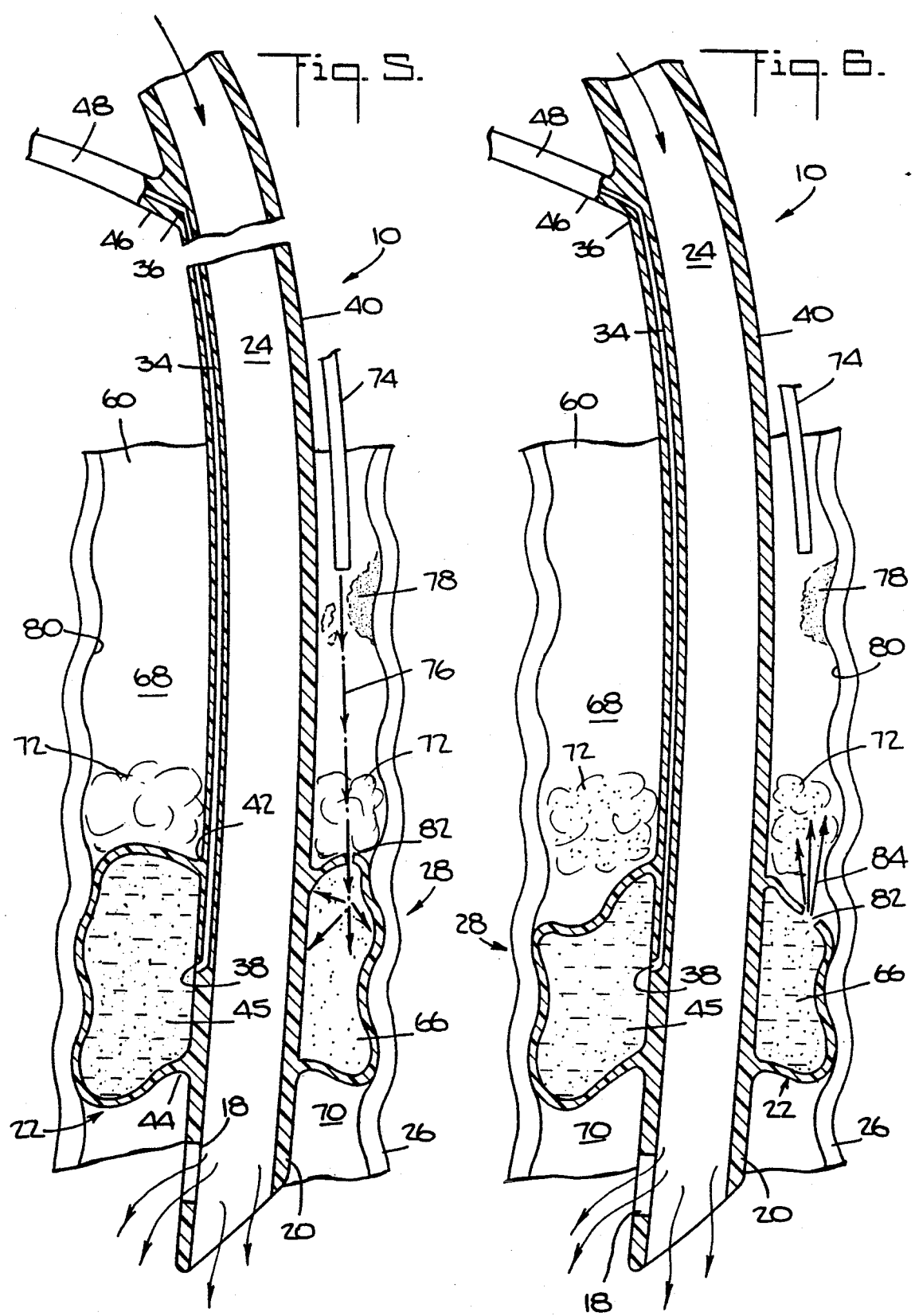

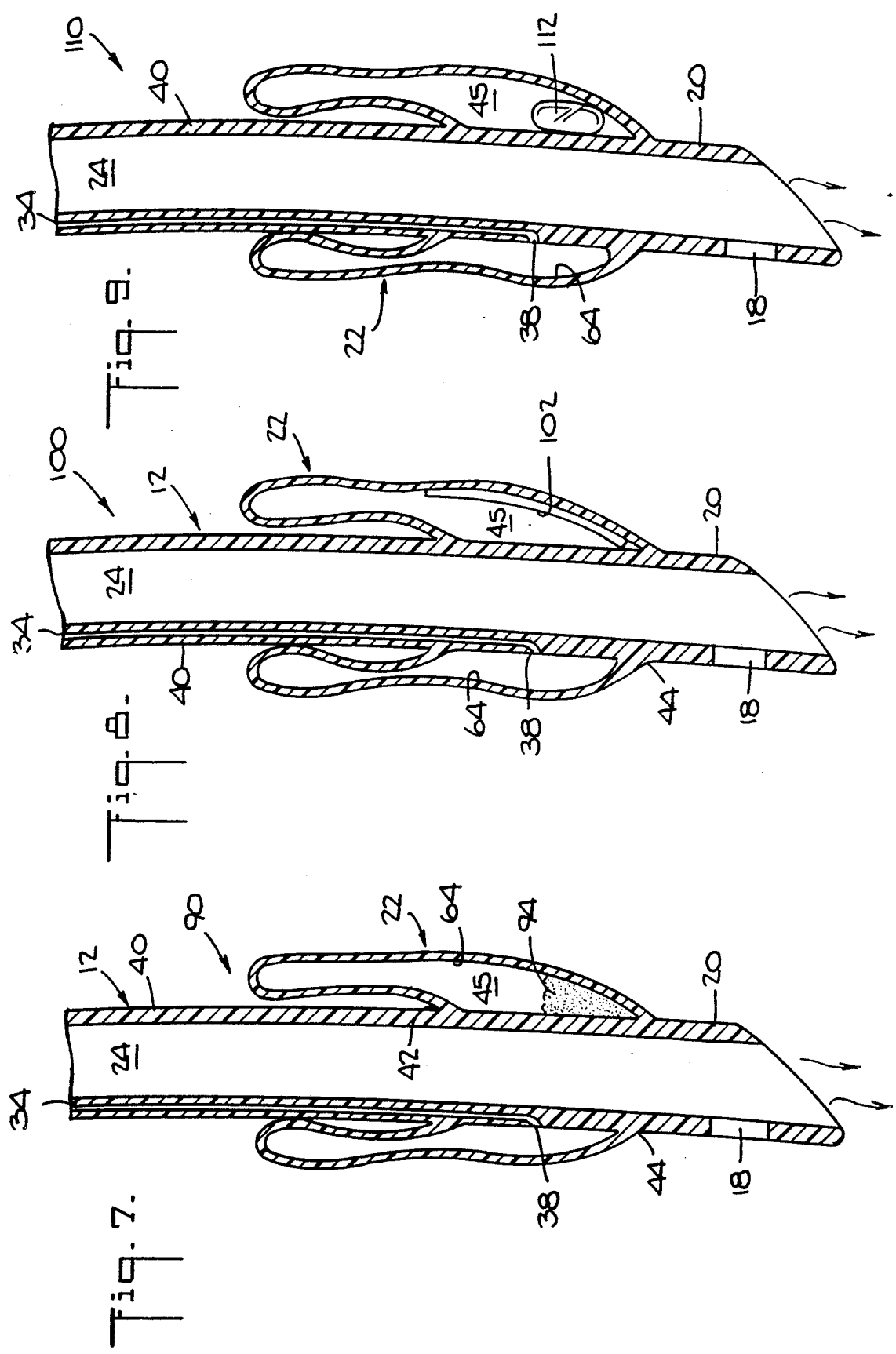

AUTOMATIC DYE DISPERSANT FOR ENDOTRACHEAL TUBES AND CATHETERS

BACKGROUND OF THE INVENTION

This invention relates to indwelling devices for passing fluids into or out of the body, especially such devices which include a stabilizing cuff, and more particularly to a device of the type described which provides a visual warning when damage occurs to the stabilizing cuff.

Endotracheal tubes and catheters are well known devices that help facilitate passage of fluid from or into the body. Although the following description is directed to endotracheal tubes, the problems described are also applicable to catheters and any other similar devices employing inflatable or expandible stabilizing cuffs.

Endotracheal tubes are usually placed in a patient's trachea during anesthesia to direct oxygen and anesthetic gas into the lungs, and to maintain a respiratory flow path during a surgical procedure.

Most endotracheal tubes include an inflatable or expandible stabilizing cuff located near a distal end of the tube. The cuff is preferably in an uninflated condition prior to installation of the tube in a body passage such as the trachea. After the tube is disposed in the trachea, the cuff is expanded with fluid such as air or saline to lodge the cuff within the passage and thereby fix the location of the endotracheal tube.

The inflation cuff can be formed of a thin sheath of flexible, expandable, biocompatible material such as silicone rubber or PVC plastic attached to the periphery of the tube to form a leak tight chamber. The typical endotracheal tube also includes an inflation lumen communicable with the cuff and noncommunicable with the main air flow passage of the tube. The inflation lumen is adapted to communicate with a supply of fluid for inflating the cuff to its expanded condition.

In many surgical procedures, especially where there is a need to perform a remote cutting operation, a laser is used to effect some portion of the tissue cutting or tissue removal. Occasionally the laser beam is inadvertently directed toward the endotracheal tube and strikes the inflation cuff. A piercing of the cuff by the laser can cause evacuation of the inflation fluid and destabilization of the cuff.

If an inflatable cuff is filled with a gas such as air, a laser strike at the cuff is likely to result in immediate evacuation of the captive air and possible ignition or smoldering of the cuff material. Oftentimes a laser strike at a cuff occurs without warning and in some instances the damage is not immediately recognized. Thus a delay in recognizing such problem inevitably results in a delayed remedy.

Since the inflation cuff is desirably formed of relatively thin expandable material, it is not feasible to incorporate laser resistant properties therein, which could adversely affect the expandability of the cuff.

One alternative to air inflation is to fill the cuff with a liquid such as saline. A saline filled cuff includes safety features that are especially desirable in a surgical environment where lasers are used. For example, if a laser strikes a saline filled cuff, the saline can extinguish or prevent laser induced ignition or smoldering of the cuff. Furthermore, an inflation cuff filled with saline can diffract a laser beam that passes through the cuff, thereby reducing the energy of the laser beam.

A further advantage of a liquid filled cuff, rather than a gas filled cuff, is that the evacuation of a liquid filled cuff, due to a laser strike, is usually slower than that of a gas filled cuff. Thus an operating team has more time to identify and remedy the problems that result from a laser strike to a cuff.

In many instances, one or more layers of cotton material, also known as neuro-sponge, are wetted and packed around the endotracheal tube distally of the inflation cuff for cooling purposes. However, such packing can camouflage a laser strike to the cuff and delay recognition of the damage caused by the laser strike.

To facilitate recognition of a pierced or otherwise damaged inflation cuff due to such inadvertencies as a laser strike, it has been suggested that methylene blue dye be added to the inflation liquid for the cuff. The methylene blue dye is understood to be an abnormal color at a surgical site and is easily recognized against body tissue, and especially against white cotton packing material. Thus methylene blue dye which issues from a cuff following a laser strike is an effective warning signal to an operating team to take whatever corrective action is necessary to remedy damage to the inflation cuff. In addition, the methylene blue dye is a medium with higher diffracting properties than saline.

Methylene blue dye is usually applied to an endotracheal cuff by initially drawing the liquid dye into an external syringe and then infusing the dye from the syringe into the cuff. Unfortunately, methylene blue dye, when supplied externally to the endotracheal tube during the intubation process, is not convenient to use since it is a staining material, and the utmost precautions must be taken to avoid leakage of such dye during intubation. Should methylene blue dye inadvertently leak and stain a receiving material around the patient during intubation, the utility of the dye would be compromised because such leakage stain might be confused with the methylene blue dye that is intended to be evacuated in the event of a laser strike at the inflation cuff.

A further problem is that additional time beyond that required for normal intubation must be taken to mix an external supply of saline with methylene blue dye and administer the dye to the endotracheal tube using whatever special precautions are necessary to assure that there is no leakage of methylene blue dye during intubation. When time is of the essence, as is usually the case in an operating room, it is not feasible to spend extra time to mix an external source of methylene blue dye with the inflation fluid immediately prior to intubation.

It is thus desirable to provide an endotracheal tube or a catheter which is capable of yielding a visual warning of inflation cuff damage without the need for an external injection source of a leak detection material during the intubation process.

OBJECTS AND SUMMARY OF THE INVENTION

Among the several objects of the invention may be noted the provision of a novel indwelling device for passing fluids into or out of the body, a novel fluid passage device with an inflatable cuff that incorporates a preinstalled warning medium to warn of damage to the cuff, a novel fluid passage device having an inflatable cuff with a pre-installed dye dispersant or leak detection material that is automatically dispersed during inflation of the cuff to provide a visual warning of any leak damage to the cuff, a novel fluid passage device having an inflatable cuff wherein a dye dispersant material is preinstalled in dry form in an inflation lumen for the cuff for automatic dispersal into the cuff during inflation of the cuff, a novel fluid passage device having an inflation cuff wherein a dye dispersant material is preinstalled in the cuff before it is inflated, and preinstalled in the inflation lumen of the cuff for automatic dispersal into the cuff during inflation, a novel fluid passage device having an inflatable cuff and a pilot balloon for inflating the cuff wherein a dye dispersant material is provided in the pilot balloon for the inflation cuff for automatic dispersal into the cuff during inflation of the cuff, a novel fluid passage device with methylene blue dye in dry form for automatic dispersal in the cuff when the cuff is inflated with liquid, and a novel method to facilitate detection of leak damage to the inflation cuff of a fluid passage device.

Other objects and features of the invention will be in part apparent and in part pointed out hereinafter.

In accordance with the invention, the fluid passage device includes a conduit, such as an endotracheal tube, having a proximal end with an inlet opening and a distal end with an outlet opening. Gases such as oxygen and anesthetic constituents are directed through a main air duct of the endotracheal tube to the outlet opening for passage into the lungs of a patient.

An inflatable cuff provided around the periphery of the endotracheal tube near the distal end is inflated through an inflation lumen that does not communicate with the main air passage of the tube.

A dye material, preferably in dry form, such as methylene blue dye is preinstalled in either or both the inflatable cuff and the inflation lumen of the endotracheal tube. In endotracheal tubes which include a pilot balloon accessible to an external supply of inflation fluid such as saline for inflating the cuff, the methylene blue dye can also be preinstalled in such balloon.

Infusion of saline solution into the pilot balloon for passage to the inflation cuff through the inflation lumen enables the methylene blue dye material to dissolve within the saline and permit the saline to take on the color of the methylene blue dye.

Thus the endotracheal tube cuff need be inflated only with saline fluid to enable the cuff to acquire the color attributes of methylene blue dye. Since the methylene blue dye is built-in or preinstalled in dry form into the cuff and/or the inflation lumen and/or the pilot balloon for inflating the cuff, there is no need to use an external source of methylene blue dye during the intubation procedure.

In some embodiments of the invention, the methylene blue dye can be coated in dry form onto the inner surface of the cuff and/or coated onto the inner surface of the inflation lumen as well as coated onto the inner surface of the pilot balloon. In other embodiments of the invention the methylene blue dye material can be provided in powder form within the cuff or within the pilot balloon as well as the inflation lumen. In another embodiment of the invention, the methylene blue dye is provided in capsule form within the cuff.

In a further embodiment of the invention the methylene blue dye is adsorbed in a porous material such as foam or paper which is installed in the cuff and/or the pilot balloon before inflation.

When inflation fluid such as saline is used for cuff inflation, the saline takes on the color characteristics of the methylene blue dye as it passes through the pilot balloon, into the inflation lumen and into the cuff. The methylene blue dye colored inflation liquid in the cuff provides an easily recognizable visual sign when piercing damage occurs to the cuff because of a laser strike, for example.

Corrective steps can thus be taken to repair or remedy the damage to the endotracheal tube. The sooner any damage to the inflatable cuff is recognized, especially with the aid of the leakage warning provided by the methylene blue dye inflation fluid within the cuff, the sooner such damage can be corrected by replacement or repair of the endotracheal tube.

The invention accordingly comprises the constructions and method hereinafter described, the scope of the invention being indicated in the claims.

DESCRIPTION OF THE DRAWINGS

In the accompanying drawings,

FIG. 1 is a simplified schematic view of a fluid passage device, such as an endotracheal tube, incorporating one embodiment of the invention and positioned in a tracheal passage;

FIG. 2 is an enlarged simplified schematic view thereof;

FIG. 3 is an enlarged fragmentary detail view thereof, partly shown in section, in the trachea with the cuff in an uninflated condition;

FIG. 4 is a view similar to FIG. 3 with the cuff in an inflated condition;

FIG. 5 is a view similar to FIG. 4 showing, in simplified schematic form, a laser device directing a laser beam toward a growth on the inside wall of the trachea and inadvertently striking the cuff;

FIG. 6 is a view similar to FIG. 5 showing evacuation of fluid from the cuff after being pierced by a laser strike; and FIGS. 7-9 show other embodiments of the invention.

Corresponding reference characters indicate corresponding parts throughout the several views of the drawings.

DETAILED DESCRIPTION OF THE INVENTION

A fluid passage device such as an endotracheal tube incorporating one embodiment of the invention is generally indicated by the reference number 10 in FIGS. 1-6.

Referring to FIG. 2, the endotracheal tube 10 includes a conduit 12 having an inlet opening 14 at a proximal end portion 16 and an outlet opening 18 at a distal end portion 20. The conduit 12 can be formed of any suitable biocompatible material such as flexible silicone and also includes a flexible, expandable cuff 22 provided near the distal end portion 20.

The inlet and outlet openings 14 and 18 communicate through a main fluid passage 24 formed within the conduit 12. The main fluid passage 24 defines a flow path for gases such as oxygen and anesthetic constituents (not shown) from the inlet opening 14 to the outlet opening 18. The outlet opening 18 directs the gas flow to a distal portion 26 of a trachea 28 that further communicates with the lung areas 30 and 32 (FIG. 1).

Referring to FIGS. 3-6, the endotracheal tube 10 further includes an inflation lumen 34 having an inlet end 36 and an outlet opening 38 formed in the wall 40 of the conduit 12. The cuff 22 surrounds the outlet opening 38 of the inflation lumen as shown in FIG. 3. A proximal edge 42 and a distal edge 44 of the cuff 22 are joined in leak tight fashion to the peripheral wall surface 40 of the conduit 12 in any suitable known manner such as by bonding with a suitable biocompatible adhesive. The cuff 22 thus forms a fluid tight chamber 45 around the outlet opening 38 of the inflation lumen 34.

The inlet end 36 of the inflation lumen 34 is joined to an end portion 46 of a flexible inflation tube 48. A pilot balloon 50 of any suitable known structure is joined to end portion 51 of the inflation tube 48.

The pilot balloon 50 is provided with a suitable known normally closed valve 52 such as a Roberts valve No. 810, made by Halkey Roberts Corporation, at an end portion 54. The valve 52 is accessible by a syringe (not shown) containing inflation fluid such as saline.

Referring to FIG. 3, a dye material such as methylene blue 62 in a dry state is coated onto an inner surface 64 of the cuff chamber 45 prior to inflation of the cuff 22.

We have found that methylene blue and most other dyes that are primarily salts do not react when presented with saline. Dyes are produced by adding the methylene blue to a brine solution which causes the dye to precipitate out. Saline being a low concentration salt water does the same to a lesser extent. Thus, there is a need for a buffer. Sodium acetate is a soluble, biocompatible buffer. Hydrochloric acid or sodium hydroxide can be used to adjust the pH to the desired predetermined level.

We have found that the higher the pH, the darker the resulting color of the dye. This is apparently due to the pH of the saline and the methylene blue solution. Preferably, the desirable pH range is close to neutral on the slightly basic side to preclude any possible patient contact with a base or acidic solution.

In preparing the saturated solution of methylene blue and deionized water with sodium acetate as a buffer, the necessary constituents are water soluble methylene blue trihydrate—USP grade, and sodium acetate trihydrate crystals—USP grade, deionized water, sodium hydroxide solution and hydrochloric acid solution.

The methylene blue dye coating 62 is formed by making a saturated solution of methylene blue and deionized water with sodium acetate as a buffer that is pH adjusted with a base or acid to reach a predetermined pH level of about 7.5 to 8.0 in accordance with the following procedure:

1. Add 2.7 grams ±0.1 grams of sodium acetate trihydrate to approximately 20 milliliters of deionized water and mix.
2. Add 5.0 grams ±0.1 grams of methylene blue trihydrate to the solution and mix well.
3. Add deionized water to reach a final volume of about 75 to 85 milliliters.
4. Mix thoroughly.
5. Measure the pH. Adjust the pH to a range of about 7.5 to 8.0 with sodium hydroxide or hydrochloric acid.
6. Transfer the solution to a 100 milliliter volumetric flask.
7. Add deionized water to reach a total 100 milliliter volume.
8. Shake vigorously and pour into a storage bottle.
9. Measure the final pH and store the bottle at room temperature, preferably for not more than 30 days.

The saturated solution can be micro-pipetted into the pilot balloon 50 before the valve 52 is installed thereon. The saturated solution is thus allowed to drain through the inflation tube 48 into the inflation lumen 34 for dispersal into the fluid tight chamber 45 of the cuff 22. The saturated solution is then allowed to dry, thereby forming a coating 62 on the surfaces within the pilot balloon 50, the inflation tube 48, the inflation lumen 34 and the cuff chamber 45. Drying of the solution can be accelerated by placing the entire endotracheal tube assembly 10 into a dry heat/air circulated oven.

After the solution has dried sufficiently, the valve 52 can be installed in the pilot balloon in any suitable known manner.

In using the endotracheal tube 10, the conduit 12 is disposed in a passage 60 of the trachea 28 of a patient in any suitable known manner such that the proximal end 16 is open to ambient air, and if required, is accessible for connection to an oxygen and anesthetic supply (not shown).

The distal end 2 of the endotracheal tube 10 is passed through the trachea 28 with the cuff 22 in an unexpanded condition to locate the distal opening 18 at a predetermined position in the trachea 28. The inflation cuff 22 is then inflated by infusion with a suitable inflation medium such as saline through the valve 52 of the pilot balloon 50. Infusion of the saline inflation medium into the pilot balloon 50 can be accomplished using a syringe (not shown). The saline inflation fluid is passed from the pilot balloon 50 through the inflation tube 48 into the inflation lumen 34 for expansion of the cuff chamber 45 of the inflation cuff 22.

As the saline inflation medium passes from the pilot balloon 50 to the cuff 22, the methylene blue dye coating is wetted by the saline, enabling the polymer containing the methylene blue dye to break down and disperse the dye into the saline. The saline inflation liquid thus takes on the color of the methylene blue dye and the dye colored saline is generally indicated by the reference number 66 in FIG. 4.

When the cuff 22 is adequately inflated a predetermined amount, such as shown for example in FIG. 4, the pilot balloon is likewise expanded a predetermined amount, and the endotracheal tube 10 and the cuff 22 are retained in a secure position within the trachea 28. The pilot balloon 50 is thus an outside indicator of the inflated condition of the cuff. However, due to the potentially slow evacuation of inflation fluid from the cuff 22 as a result of a laser strike, the pilot balloon 50 does not provide an adequately quick indication of damage to the cuff 22.

It will be noted that the inflated condition of the cuff 22, as shown in FIG. 4, prevents passage of gas through the tracheal passage 60 from a proximal side 68 of the cuff 22 to a distal side 70 of the cuff 22. Thus, gas or air can only pass to the distal side 70 of the inflation cuff 22 through the fluid passage 24 of the endotracheal tube 10. Cotton packing 72 such as neuro-sponge can thus be provided at the proximal side of the cuff 22.

During surgery, a laser device 74 such as shown in simplified schematic form in FIG. 5, is used to perform a surgical procedure. In a hypothetical procedure described herein for illustrative purposes only, the laser device 74 emits a laser beam 76 directed at a growth 78 that is to be surgically removed from the inner wall surface 80 of the trachea 28.

Should the laser beam 76 strike the cuff 22 a shown in FIG. 5, a piercing hole 82 can result through which the dye colored saline 66 can escape. Evacuation of the dye colored saline 66 from the cuff 22 is schematically indicated at 84 and passes into the cotton packing 72, thereby staining the cotton packing such that the laser damage to the cuff 22 becomes visually recognizable to an operating team via the stained cotton.

Steps can then be taken to make the necessary repair or replacement of the endotracheal tube 10.

A further embodiment of the endotracheal tube is generally indicated by the reference number 90 in FIG. 7. The endotracheal tube 90 is essentially similar to the endotracheal tube 10 as indicated by corresponding reference characters. However the endotracheal tube 90 includes a porous material 92 having methylene blue dye and buffer solution previously described adsorbed therein. The porous material which adsorbs the methylene blue and the buffer and retains the solution in a dry state can be a foam such as, for example, polyester or polyurethane open cell foam, or paper.

For example, a piece of 5/16" by ⅛ polyester/polyurethane open cell foam 92 is saturated in deionized water and the foam 92 is squeezed to remove excess water. The moist foam piece 92 can be placed into the pilot balloon 50 (FIG. 1) before the valve 52 is installed. The methylene blue/sodium acetate buffer solution is added to the foam piece 92 using a micropipette, for example (not shown). The foam piece 92 can be squeezed through the walls of the pilot balloon 50 to ensure that the solution is adsorbed.

If desired, the conduit 48 and the pilot balloon 50 can be detached from the conduit 12 during this procedure. Thus the inflation tube 48 and the pilot balloon 50 with the sponge 92 installed therein can be placed in a dry heat/air circulated oven to dry. When drying is completed, the inflation subassembly, namely the pilot balloon 50 and the inflation tube 48, can be connected to the conduit 12. If desired, a similar sponge piece 94, which is treated in a manner similar to that previously described for the sponge piece 92, can be provided in the cuff chamber 45 before the cuff 22 is bonded to the conduit 12.

Thus, when saline fluid is infused into the pilot balloon 50 and into the cuff 22 in a manner similar to that previously described for the device 10, the methylene blue dye dissolves and is released from the porous material 92 and 94 dispersing throughout the cuff 22.

Another embodiment of the endotracheal tube is generally indicated by the reference number 100 in FIG. 8. The endotracheal tube 100 is essentially similar to the endotracheal tube 10 of FIGS. 1-6. However, the methylene blue and buffer material can be disposed in the cuff chamber 45 in powder form as indicated by the reference number 102. The methylene blue/buffer solution previously disclosed can be formed as a powder by mixing in a dry state the methylene blue and the needed buffers, and dispersed through the pilot balloon before the valve 52 is installed, for deposition in the inflation cuff chamber 45. The valve 52 is then installed onto the pilot balloon.

The device 100 is used in a manner similar to that previously described for the device 10. Thus, when the saline inflation fluid is infused past the valve 52 into the pilot balloon 50 for dispersal into the inflation cuff 22, the methylene blue dye disperses throughout the saline fluid which expands the cuff 22.

Still another embodiment of the endotracheal tube is generally indicated by the reference number 110 in FIG. 9. The endotracheal tube 110 is substantially similar to the endotracheal tube 10 of FIGS. 1-6. However, the methylene blue dye/buffer material can be incorporated in capsule or a pellet form in the inflation cuff chamber 45 as indicated at reference number 112. The capsule form of the methylene blue dye and buffer can be made from the previously described methylene blue dye/buffer solution by mixing the dye and buffer in a dry state and placing it in a water soluble capsule.

The capsule 112 is then installed in the inflation cuff chamber 45 before the inflation cuff 22 is bonded to the conduit 12. A corresponding capsule or pellet 113 (FIG. 1) can also be provided in the pilot balloon 50. Thus, introduction of saline inflation fluid into the pilot balloon 50 causes the capsule 113 therein to dissolve and disperse dye material throughout the saline that eventually reaches the cuff 22. The capsule 112 within the cuff chamber 45 is also dissolved by the saline to supplement the intensity of the color produced within the pilot balloon 50. Thus the introduction of saline inflation fluid into the inflation cuff 22 causes the capsules 112 and 113 to dissolve and disperse dye material throughout the cuff chamber 45. In this manner, the device 110 is capable of providing a warning to alert a surgical team of damage to the cuff 22 in a manner similar to that previously described for the embodiment 10.

Although the embodiments of the invention illustrated and described herein are endotracheal tubes, the provision of the methylene blue dye/buffer leak detection material also referred to as dye dispersant material is similarly applicable to a catheter or other device having a stabilizing cuff in a body passage.

In such devices the methylene blue dye/buffer material is incorporated in a manner similar to that previously described for the endotracheal tube cuff. It is contemplated that other suitable dye dispersant materials can be used such as PVPs, PVAs, collagens and other water soluble and biocompatible colorants such as FDA approved food colorants.

Some advantages of the present invention evident from the foregoing description include an endotracheal tube or catheter wherein a leak detection material in dry form is preinstalled before inflation of a cuff. Thus the need for external incorporation of a leak detection material with an inflation medium that is used to inflate the cuff is unnecessary, and the possibility of external staining or discoloration during the installation of the endotracheal tube is eliminated. Since the leak detection material is preinstalled in the endotracheal tube there is no need to engage in extra steps for incorporation of the methylene blue dye in the cuff.

Once the methylene blue dye is preinstalled in the endotracheal tube it can be sterilized while in a dry state. Thus possible contamination of an endotracheal tube by external infusion of liquid methylene blue dye for inflation purposes is avoided.

A further advantage is that an inflation cuff for a fluid passage tube with a preinstalled signaling capability can be inflated as easily as an inflation cuff that does not have the same signaling capability.

In view of the above, it will be seen that the several objects of the invention are achieved and other advantageous results attained.

As various changes can be made in the above constructions and method without departing from the scope of the invention it is intended that all matter contained in the above description or shown in the accompanying drawings shall be interpreted as illustrative and not in a limiting sense.

What is claimed is:

1. An endotracheal tube having a conduit with a main air flow passage, an inflation lumen formed in said conduit noncommunicable with said main air flow passage, a pilot balloon communicable with said inflation lumen, an expandable inflation cuff jointed to said conduit for inflation by a liquid infused through said inflation lumen, and a preinstalled leak detection dye material provided in said pilot balloon in dry form adapted for dispersal in said cuff responsive to infusion of said liquid through said pilot balloon and into said cuff.

2. The endotracheal tube as claimed in claim 1 wherein said liquid dye detection material is preinstalled in said cuff in dry form.

3. The endotracheal tube as claimed in claim 2 wherein said leak detection dye material includes methylene blue.

4. A method to facilitate detection of leakage from the cuff of an endotracheal tube or catheter having an inflation lumen including,
   a. preinstalling a dry dye dispersant material to be dissolved in the cuff or inflation lumen of the endotracheal tube or catheter before inflating the cuff and,
   b. thereafter inflating the cuff with a liquid inflation material to dissolve the dye dispersant material such that the inflation fluid in the cuff takes on the color of the dye dispersant material.

5. The method of claim 4 wherein the step of preinstalling includes disposing the dry dye dispersant material in a pilot balloon of the endotracheal tube or catheter.

6. The method of claim 5 wherein the step of preinstalling includes disposing the dry dye dispersant material in the cuff or pilot balloon in the form of a powder, pellet, coating or an adsorbed constituent of a porous material.

7. The method of claim 4 wherein the step of preinstalling includes disposing the dry dye dispersant material in the inflation lumen.

8. The method of claim 4 wherein the dry dye dispersant material is provided with a buffer.

9. The method of claim 8 wherein the dry dye dispersant material is a combination of methylene blue and a buffer of sodium acetate.

10. In combination, a tube having opposite end portions and a fluid flow lumen for conducting the flow of fluid from one of the end portions to the other end portion, said tube being provided with an inflation lumen noncommunicable with said fluid flow lumen for passage of liquid inflation fluid, and a flexible inflatable cuff joined to a predetermined peripheral surface portion of said tube for fluid inflation from a substantially collapsed condition to a substantially expanded condition to lodge said cuff and said tube in a substantially fixed position in a body passage while said cuff is in said inflated condition, said cuff including a dye dispersant material in powder form, said dye dispersant material being a material which dissolves in said liquid inflation fluid to form a liquid having a distinctive color for us in inflating said cuff.

11. The combination as claimed in claim 10 wherein the dye dispersant material is methylene blue.

12. The combination as claimed in claim 1, wherein said dye dispersant material includes a buffer.

13. The combination as claimed in claim 12 wherein the dye dispersant material includes a combination of methylene blue with a buffer of sodium acetate.

14. The combination, a tube having opposite end portions and a fluid flow lumen for conducting the flow of fluid from one of the end portions to the other end portion, said tube being provided with an inflation lumen noncommunicable with said fluid flow lumen for passage of liquid inflation fluid, and a flexible inflatable cuff joined to a predetermined peripheral surface portion of said tube for fluid inflation from a substantially collapsed condition to a substantially expanded condition to lodge said cuff and said tube in a substantially fixed position in a body passage while said cuff is in said inflated condition, said cuff including a dye dispersant material in pellet form, said dye dispersant material being material which dissolves in said liquid inflation fluid to form a liquid having a distinctive color for use in inflating said cuff.

15. In combination, a tube having opposite end portions and a fluid flow lumen for conducting the flow of fluid from one of the end portions to the other end portion, said tube being provided with an inflation lumen noncommunicable with said fluid flow lumen for passage of liquid inflation fluid, and a flexible inflatable cuff joined to a predetermined peripheral surface portion of said tube for fluid inflation from a substantially collapsed condition to a substantially expanded condition to lodge said cuff and said tube in a substantially fixed position in a body passage while said cuff is in said inflated condition, said cuff having an inner surface and a dye dispersant material as a coating on said inner surface, said dye dispersant material being a material which dissolves in said liquid inflation fluid to form a liquid having a distinctive color for use in inflating said cuff.

16. In combination, a tube having opposite end portions and a fluid flow lumen for conducting the flow of fluid from one of the end portions to the other end portion, said tube being provided with an inflation lumen noncommunicable with said fluid flow lumen for passage of liquid inflation fluid, and a flexible inflatable cuff joined to a predetermined peripheral surface portion of said tube for fluid inflation from a substantially collapsed condition to a substantially expanded condition to lodge said cuff and said tube in a substantially fixed position in a body passage while said cuff is in said inflated condition, said cuff including a porous material, a dye dispersant material, said dye dispersant material loaded in said porous material, said dye dispersant material being a material which dissolves in said liquid inflation fluid to form a liquid having a distinctive color for use in inflating said cuff.

17. The combination as claimed in claim 16 wherein said porous material is a foam material.

18. The combination as claimed in claim 16 wherein said porous material is paper.

19. In combination, a tube having opposite end portions and a fluid flow lumen for conducting the flow of fluid from one of the end portions to the other end portion, said tube being provided with an inflation lumen noncommunicable with said fluid flow lumen for passage of liquid inflation fluid, and a flexible inflatable cuff joined to a predetermined peripheral surface portion of said tube for fluid inflation from a substantially collapsed condition to a substantially expanded condition to lodge said cuff and said tube in a substantially fixed position in a body passage while said cuff is in said inflated condition, said inflation lumen having an inner surface and a dye dispersant material as a coating on said inner surface, said dye dispersant material being a material which dissolves in said liquid inflation fluid to form a liquid having a distinctive color for use in inflating said cuff.

20. In combination, a tube having opposite end portions and a fluid flow lumen for conducting the flow of fluid from one of the end portions to the other end portion, said tube being provided with an inflation lumen noncommunicable with said fluid flow lumen for passage of liquid inflation fluid, and a flexible inflatable cuff joined to a predetermined peripheral surface portion of said tube for fluid inflation from a substantially collapsed condition to a substantially expanded condition to lodge said cuff and said tube in a substantially fixed position in a body passage while said cuff is in said inflated condition, said cuff including a pilot balloon, said pilot balloon having a dye dispersant material therein, said dye dispersant material being a material which dissolves in said liquid inflation fluid to form a liquid having a distinctive color for infusing said pilot balloon and thereby inflating said cuff.

21. In combination, a tube having opposite end portions and a fluid flow lumen for conducting the flow of fluid from one of the end portions to the other end portion, said tube being provided with an inflation lumen noncommunicable with said fluid flow lumen for passage of liquid inflation fluid, and a flexible inflatable cuff joined to a predetermined peripheral surface portion of said tube for fluid inflation from a substantially collapsed condition to a substantially expanded condition to lodge said cuff and said tube in a substantially fixed position in a body passage while said cuff is in said inflated condition, said cuff having an inflation lumen, said inflation lumen including a dye dispersant material therein in a form selected from the group consisting of powder, pellet, coating and an adsorbed constituent of a porous material, said dye dispersant material being a material which dissolves in said liquid inflation fluid to form a liquid having a distinctive color for use in inflating said cuff.

22. In combination, a tube having opposite end portions and a fluid flow lumen for conducting the flow of fluid from one of the end portions to the other end portion, said tube being provided with an inflation lumen noncommunicable with said fluid flow lumen for passage of liquid inflation fluid, and a flexible inflatable cuff joined to a predetermined peripheral surface portion of said tube for fluid inflation from a substantially collapsed condition to a substantially expanded condition to lodge said cuff and said tube in a substantially fixed position in a body passage while said cuff is in said inflated condition, said cuff including a pilot balloon, said pilot balloon having a dye dispersant material therein, said dye dispersant material being in the form selected from the group consisting of powder, pellet, coating and an adsorbed constituent of a porous material said dye dispersant material being a material which dissolves in said liquid inflation fluid to form a liquid having a distinctive color for use in inflating said cuff.

* * * * *